(12) United States Patent
Küper

(10) Patent No.: US 8,103,012 B2
(45) Date of Patent: Jan. 24, 2012

(54) ELECTROMECHANICAL SPEECH AID

(75) Inventor: Martin Küper, Grevenbroich (DE)

(73) Assignee: Servona GmbH, Troisdorf (DE)

( * ) Notice: Subject to any disclaimer, the term of this patent is extended or adjusted under 35 U.S.C. 154(b) by 660 days.

(21) Appl. No.: 12/296,010

(22) PCT Filed: Feb. 22, 2007

(86) PCT No.: PCT/EP2007/051723
§ 371 (c)(1),
(2), (4) Date: Jan. 26, 2009

(87) PCT Pub. No.: WO2007/113056
PCT Pub. Date: Oct. 11, 2007

(65) Prior Publication Data
US 2009/0171460 A1 Jul. 2, 2009

(30) Foreign Application Priority Data
Apr. 4, 2006 (EP) .................................. 06112214

(51) Int. Cl.
*A61F 2/20* (2006.01)
(52) U.S. Cl. ............................................. 381/70; 623/9
(58) Field of Classification Search .................. 381/70, 381/151, 326, 396; 623/9
See application file for complete search history.

(56) References Cited

U.S. PATENT DOCUMENTS

| | | | |
|---|---|---|---|
| 3,978,286 A | 8/1976 | Watson | |
| 4,028,492 A | 6/1977 | Sickel | |
| 5,812,681 A * | 9/1998 | Griffin | 381/70 |
| 6,252,966 B1 * | 6/2001 | Griffin | 381/70 |
| 6,359,988 B1 * | 3/2002 | Espy-Wilson | 381/70 |
| 6,735,315 B1 * | 5/2004 | Ifukube et al. | 381/70 |
| 7,212,639 B1 * | 5/2007 | Houston | 381/70 |
| 2003/0031326 A1 | 2/2003 | Lukacovic | |

FOREIGN PATENT DOCUMENTS

DE 3529553 2/1987

OTHER PUBLICATIONS

International Search Report for corresponding application No. PCT/EP2007/051723.
International Preliminary Report on Patentability for corresponding application No. PCT/EP2007/051723.

* cited by examiner

*Primary Examiner* — Kevin M Picardat
(74) *Attorney, Agent, or Firm* — Renner, Otto, Boisselle & Sklar, LLP

(57) ABSTRACT

An electromechanical system for the stimulating of vibration of biological tissue, particularly of the human throat tissue, is provided with an electromechanical converter (12) having a self-resonant frequency and being operative for converting electric energy into mechanical energy, designed as a linearly movable, driven element (14) arranged to osculate about a zero-point position or from a zero-point position into a positive or negative direction, and with a vibration surface (20) for acting on the biological tissue. The driven element (14) of the electromechanical converter (12) is supported by an elastic, resilient unit (24) having a self-resonant frequency above the self-resonant frequency of the electromechanical converter (12), whereby the vibration surface (20) is caused to oscillate across a certain frequency range with a swing which at a constant input voltage is substantially constant across the frequency.

13 Claims, 1 Drawing Sheet

ELECTROMECHANICAL SPEECH AID

Figure 1:
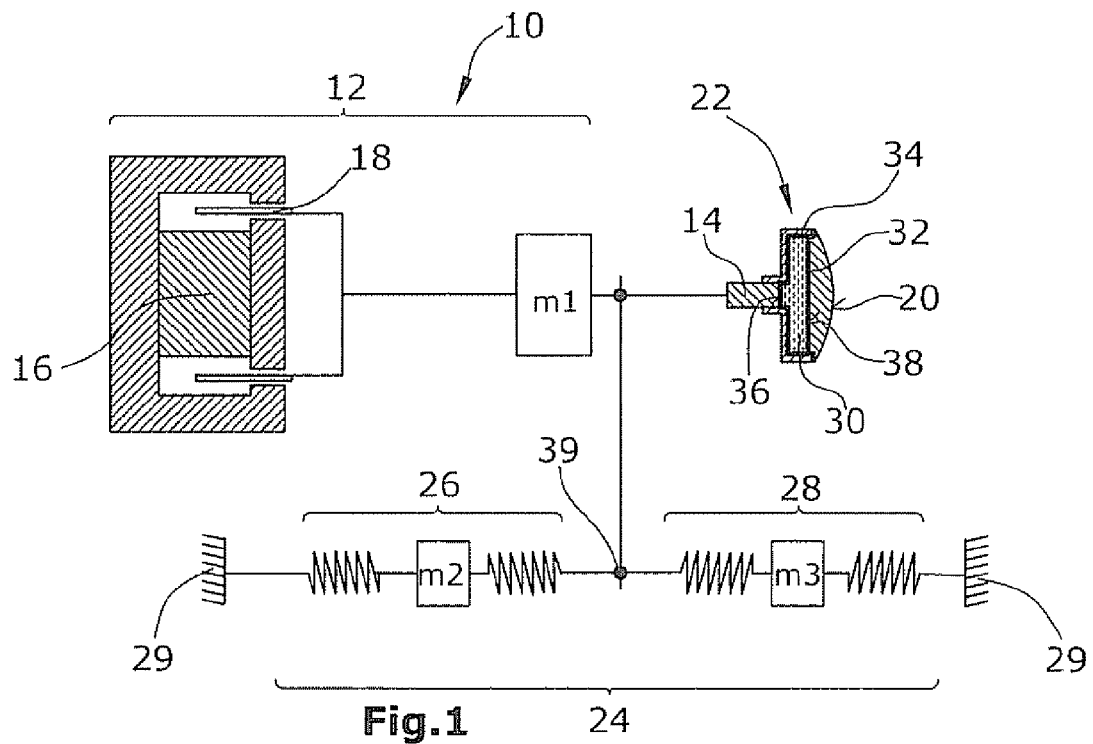

This application is a national phase of International Application No. PCT/EP07/051723 filed Feb. 22, 2007 and published in the English language.

The present invention relates to an electromechanical system for the stimulating of vibration of biological tissue, particularly of tissue of the human throat.

It is already known to use so-called speech aids so that laryngectomy or tracheotomy patients will still be able to articulate themselves by spoken language. These speech aids are electromechanical systems comprising a vibration surface which is pressed against the tissue of the throat and thus causes the throat tissue to vibrate, thereby causing also the air in the pharynx and in the oral cavity to vibrate. By use of the remaining natural organs of speech (connecting pipe), the patient will then be able to pronounce words and syllables, possibly after a suitable training.

Speech aid are described, e.g., in DE-C-35 29 553, U.S. Pat. No. 3,978,286, U.S. Pat. No. 4,028,492, inter alia. Known speech aids comprise a hard shell or a similar reverberant surface which, by means of a striker member to be operated electromechanically (e.g. by a magnet/coil system), is excited in a pulsed manner and thus will oscillate according to its self-resonance. As a result, the voice of a person using this known speech aid has a rather mechanical and monotonous sound.

It is the object of the invention to provide an electromechanical system for the stimulating of vibration of biological tissue, particularly of tissue of the human throat, wherein the electromechanical system is capable of sound variation so that the generated speech has a more natural human sound.

According to the present invention, the above object is achieved by an electromechanical system for the stimulating of vibration of biological tissue, which system comprises:

an electromechanical converter having a self-resonant frequency and being operative for converting electric energy into mechanical energy at a linearly movable, driven element arranged to oscillate about a zero-point position or from a zero-point position into a positive or negative direction, and a vibration surface for acting on the biological tissue, the driven element of the electromechanical converter being operatively coupled to the vibration surface and being supported by an elastic, resilient unit having a self-resonant frequency above the self-resonant frequency of the electromechanical converter, whereby the vibration surface is caused to swing across a frequency range of which the upper limit is above the self-resonant frequency of the electromechanical converter and is equal to or smaller than the self-resonant frequency of the elastic, resilient unit, the oscillation of the vibration surface being performed with a swing which at a constant input voltage is substantially constant across the frequency.

For the inventive functioning of a speed aid, it is required that, across a largest possible frequency range, there is available a constant and largest possible swing of the oscillation surface abutting the tissue of the throat. In practice, it has been revealed that vibrational excitations of the throat tissue of up to 1,500 Hertz will suffice. Thus, in the frequency spectrum up to 1,500 Hertz, there should exist a large swing which is as constant as possible and independent of the frequency.

In electromechanical systems, the swing of an oscillating element below the self-resonance of the system is substantially constant across the frequency. Additionally, it is to be noted that large swings can be generated if the self-resonance and the resonance frequency, respectively, are low, which goes along with a "soft support" of the oscillating element. The force which the drive unit of the electromechanical system can transmit to an impedance converter of the electromechanical system will be all the larger the less force is required to generate a swing. Under this aspect, a soft support is of advantage.

However, a soft support also means that the resonant frequency is relatively low and the transmission range is thus relatively small; notably, it is only the range below the self-resonance of the electromechanical system which can be used as the transmission range. Thus, in order to obtain a transmission range which extends up to a relatively high self-resonance of about 1.5 kHz, the drive unit must have a relative high self-resonance. A high self-resonance, however, has the effect that the support must be relatively stiff, which in turn causes a relatively low resilience and thus a smaller swing.

The electromechanical system of the invention comprises a drive unit, i.e. an electromechanical converter for converting electromechanical energy into mechanical energy. This electromechanical converter is operatively connected to a vibration surface for acting on the human tissue. The electromechanical converter is effective to cause the vibration surface to oscillate around a zero-point position or, for instance, with the vibration surface pressed against the tissue, from a zero-point position into a positive or negative direction.

According to the invention, the driven element of the electromechanical converter will now be engaged by an elastic, resilient unit for support of the drive element, wherein this unit as such has a self-resonant frequency above the self-resonant frequency of the electromechanical converter. Thus, the vibration surface can oscillate across a frequency range of which the upper limit is above the self-resonant frequency of the electromechanical converter and is equal to or smaller than the self-resonant frequency of the elastic, resilient unit, the oscillation of the vibration surface being performed with a swing which at a constant input voltage is substantially constant across the frequency (provided that the vibration surface is coupled to the biological tissue and is pressed thereagainst by a force of e.g. 4 to 7 N which is realistic in practice). In this regard, the driven element itself can comprise the vibration surface or be coupled to the same. However, this coupling, i.e. the abutment, can be brought about only if the vibration surface is pressed against the throat tissue with a force which is sufficient for obtaining the desired effect of the overall system as a speech aid. This has the advantage that, when the system has been removed from the tissue, the vibration surface of the system is not excited and the radiated noises are thus reduced.

With the aid of the inventive configuration, it is also possible to utilize electromechanical drive units such as e.g. magnetorestrictive or electroacoustic converters which have a relatively low self-resonance. Thus, one can use a drive unit with soft support, with the resultant advantage that large swings can be generated by relatively low forces. To make it possible now to generate such a large swing also in case of frequencies above the self-resonance of the drive unit, the invention provides that, in parallel to the drive unit and the vibration surface, there is arranged an elastic, resilient unit for supporting and centering the driven element; the self resonant frequency of this unit is substantially identical to the highest frequency at which the electromechanical system is to be operated. In this manner, it is accomplished that the overall system will operate with an approximately constant and relatively large swing of its vibration surface.

According to an advantageous embodiment of the invention, it is provided that the elastic, resilient unit is coupled with a mechanical bias to the driven element of the electromechanical converter so that the driven element is biased in the direction towards the vibration surface.

Further, it can be suitably provided that the elastic, resilient unit comprises at least one spring element. Generally, this spring element can be any possible type of a (centering) spring element (for a linearly movable oscillating element) of a material which is suitable for such spring elements; these can be cup springs, leaf springs, spiral springs acting laterally of their extension plane, or membrane-type supports. Coil springs, however, are particularly useful for spring elements.

According to a further advantageous embodiment of the invention, it is provided that the elastic, resilient unit comprises a first spring element and a second spring element which are coupled to each other, at least one of the spring elements serving to bias the driven element of the electromechanical converter.

The elastic, resilient unit is provided for centering the electromechanical converter and the driven element of the electromechanical converter, respectively. If the centering of the drive unit is performed by means of an elastic, resilient unit as provided by the invention, the centering is brought about by using not merely "resiliency" effect but a whole system of resiliency and additional self-resonance, i.e. the self-resonance of the elastic, resilient system which is all the larger the larger the bias generated by the elastic, resilient unit is.

According to a further advantageous embodiment of the invention, the driven element of the electromechanical converter and the vibration surface have arranged therebetween an impedance converter (e.g. of the pneumatic or hydraulic type) for adapting the amount of the oscillating swing of the vibration surface to the biological tissue, wherein the impedance converter can be excited at its input side by the electromechanical converter and by the driven element of the latter, respectively; on its output side, on the other hand, the converter will excite the vibration surface. With the aid of this impedance converter, the swing of the vibration surface, i.e. the radiation resistance of the electromechanical system, can be adapted to the radiation resistance of the medium into which the vibrations are to be coupled. Thus, should the electromechanical converter or its driven element in combination with the elastic, resilient unit not excite the vibration surface in the optimum manner provided for the coupling of energy into the medium (biological tissue or particularly throat tissue), the impedance converter can be put to use for adapting the radiation resistance so that the vibration energy can be effectively transmitted into the biological tissue.

Suitably, the impedance converter has its input side provided with an input surface which can be excited by the driven element of the electromechanical converter or by the elastic, resilient unit, and has its output side provided with an excited output surface, which surfaces are operatively coupled to each other by an incompressible fluid (gas or liquid, gel, silicone, a viscous medium or another material which is incompressible in the transmission range of interest and is capable of changing its shape). Both surfaces of the impedance converter should be flexible or movable (rigid or elastic). A suitable realization resides in the containment of the incompressible fluid within a closed membrane surface which is encapsulated by a surrounding body, while regions defining the input and output surfaces are left free.

To make it possible to change the swing of the vibration surface or of the impedance converter, the impedance converter comprises input and output surfaces of different sizes. Thus, for instance, for increasing the swing of the vibration surface, the output surface of the impedance converter is selected to be larger than the input surface thereof. Conversely, the input surface of the impedance converter has to be selected to be larger than the output surface thereof if the swing generated by the electromechanical system without impedance converter is to be reduced. Using the impedance converter, it is also possible to adapt a modular electromechanical system for optimum transmission of the available mechanical power of the drive unit to the respective medium for which the electromechanical system is used to excite the vibration.

In this context, it is to be noted that the features of the impedance converter do not necessarily have to be combined with the elastic support of the driven element according to claim 1. Instead, the features of the impedance converter constitute independent features of a speech aid which can be realized also if the driven element coupled to the input side of the impedance converter is not elastically supported and centered, respectively. Thus, for instance, the driven element could be arranged for linear movement without being centered along its longitudinal path of displacement.

Therefore, in the field of speech aids for laryngectomized patient or patients who underwent larynx surgery, it is according to the present invention for the first time proposed to excite the vibration surface across a range of frequencies. Up to now, the vibration surface of speech aids has been acted on—by means of a striker element—merely in a pulsed manner such as is the case with a bell. Thus, the swing of the vibration surface has been determined by its self-resonance or the self-resonance of the element having the vibration surface formed thereon. Variation of the sound has thus been precluded. With the present invention, however, this prior art approach is completely abandoned and, at least during the operation of the speech aid, a permanent coupling of the vibration-generating element to the vibration surface is accomplished. Thus, it is now rendered possible to introduce different frequencies into the vibration surface so that the vibration surface is enabled to swing across a range of frequencies. In concrete use, a frequency range of several 10 Hertz up to about 1,500 Hertz has been found practicable. Thereby, the patient's voice is allowed to assume a human sound instead of the rather tinny sound of previously known speech aids.

The present invention also relates to the use of an electromechanical system as described above by a person who underwent laryngectomy or tracheotomy, for generating speech sounds by applying the vibration surface to the throat tissue of the person in such a manner that the driven element is coupled to the vibration surface.

Finally, the present invention also comprises a method for generating speech sounds, to be used by a person who underwent laryngectomy or tracheotomy, said method comprising:

applying an electromechanical system as described above by its vibration surface to the throat tissue of the person in such a manner that the driven element is coupled to the vibration surface, and forming the mouth cavity and/or moving the mouth, lips and tongue by the person in a suitable manner for generating speech sounds.

An embodiment of the invention will be described in greater detail hereunder with reference to the accompanying drawings. In the drawings—

Figure 2:
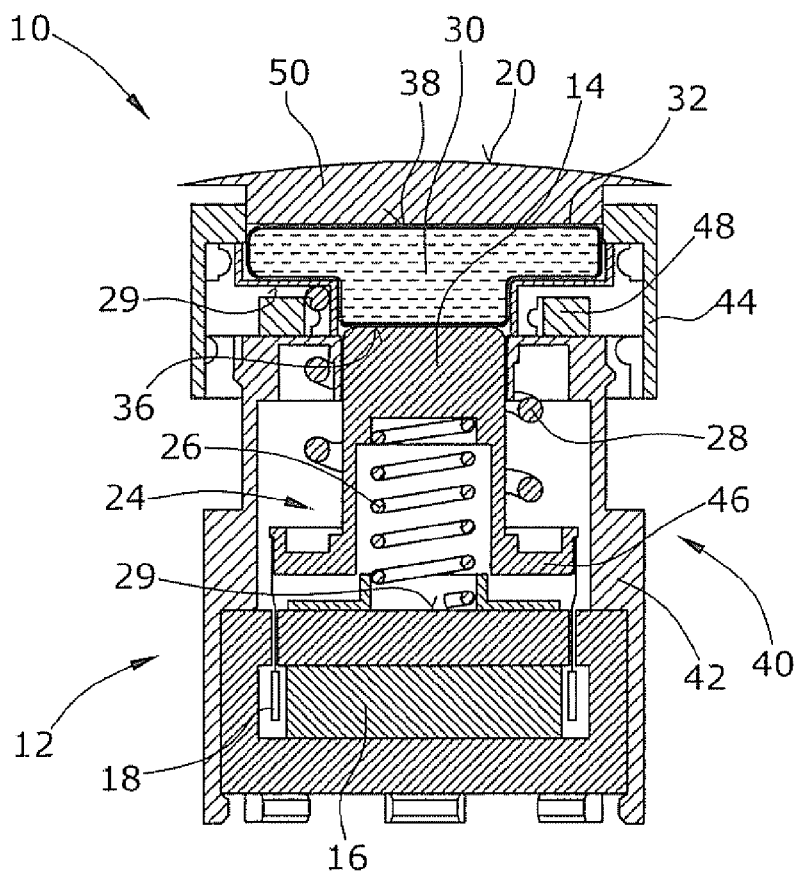

FIG. 1 is a diagrammatic sketch of the essential functional components of the electromechanical system according to an embodiment of the invention, and FIG. 2 is a longitudinal sectional view illustrating the configuration of the electromechanical system of FIG. 1, to the effect that the system can be used for exciting the vibrations of the human throat tissue.

FIG. 1 shows a schematic view of the arrangement and the coordinated operation of the diverse components and functional blocks of an electromechanical system 10 provided for exciting the vibrations of the human throat tissue. The electromechanical system 10 comprises an electromechanical converter 12 including a driven element 14 having a mass m1. The electromechanical converter 12 comprises a magnetic system 16 with a coil 18 arranged therein which has current flowing therethrough and is arranged to reciprocatingly move the driven element 14. The driven element 14 in turn is coupled to a vibration surface 20 which via an intermediate impedance converter 22 is operatively connected to the driven element. In the present embodiment, the electromechanical converter 12 is designed as an electroacoustic converter comprising e.g. an plunger coil and a magnet system. The plunger coil can be provided directly as a driven element or be connected to such an element, the latter being the case in the present embodiment.

According to the invention, for centering the electromechanical converter 12 and the driven element 14 of the electromechanical converter 12, respectively, there is used an elastic, resilient unit 24 which in the present embodiment comprises two coil springs 26,28 which have oscillatory masses m2 and m3, respectively, and which are connected parallel to the driven element 14. The two coil springs 26,28 are connected to each other and are arranged to support each other, on their mutually averted ends, on abutment portions 29. The connection point 39 of the two coil springs 26,28 has the driven element 14 of the electromechanical converter 12 mechanically coupled thereto. By the configuration of the two coil springs 26,28 and/or their bias, a "resiliency" can now be lent to the centering of the driven element 14, wherein this centering system additionally includes at least one self-resonance (determined by the springs 26,28) which will be all the larger the larger the bias of the springs 26,28 is.

As already mentioned above, the impedance converter 22 is connected between the electromechanical converter 12 and the vibration surface 20. With the aid of this impedance converter 22, the swing executed by the driven element 14 can be influenced with regard to its effect on the swing of the vibration surface 20. The impedance converter 22 is provided as a membrane bag 32 filled with an incompressible fluid 30 and surrounded by a receiving body 34 in an annular configuration. Within this body 34, the membrane bag 32 is exposed on an input surface 36 and an output surface 38. Depending on the selection of the size ratio between these two surfaces, the swing of the driven element 14 can be converted into a higher swing of the vibration surface 20 or into a lower swing of the vibration surface.

FIG. 2 shows an example of a possible realization of the electromechanical system 10 according to FIG. 1. This example comprises a housing 40 with a first housing portion 42 and a second housing portion 44. The first housing portion 42 accommodates the magnetic core 16, the coil 18 and the driven element 14 provided as a plunger. The plunger is provided with a coil-receiving flange 46 connected to coil 18. Also accommodated in the first housing portion 42, apart from the electromechanical converter 12, is the elastic, resilient unit 24. In FIG. 2, also the coil springs 26 and 28 are shown, wherein the coil spring 26 is supported on the magnetic core 16 serving as a fixed abutment 29 and the coil spring 28 is supported on the first housing portion 42 or on a holding element 48 connected thereto as a fixed abutment 29.

Further, both coil springs 26,28 are in engagement within the plunger. Thus, with the aid of the elastic, resilient unit 24, the plunger is centered.

The driven element 14 (plunger) of the electromechanical converter 12 is contacted by the input face 36 of the fluid-filled membrane bag 32 of impedance converter 22 while the output face 38 of the impedance converter 22 is arranged in contact with a tissue excitation element 50 comprising the vibration surface 20. The tissue excitation element 50 and the impedance converter 22 are accommodated in the second housing element 44.

In the present embodiment, the electromechanical converter 12, generating a large swing with little force, is used as a drive unit. The mechanical performance (force×swing) is converted by impedance converter 22 into a smaller swing of the vibration surface 20 or of the swinging tissue excitation element 50 with large force.

The essential aspects of the present invention will be stressed once more hereunder.

Each electromechanical system has a swing, below its self-resonance, which is not dependent on the frequency, i.e. a swing which is constant throughout the frequency. If the resonant frequency is low, which is effected by a "soft" support, large swings can be generated. The force which the drive unit is able to transmit to the impedance converter will be the larger the less force will be required for generating the swing. Therefore, a soft support is of advantage. A soft support, however, means that the frequency transmission range within which the swing is constant, will be merely small since only the range below the self-resonance of the electromechanical system can be used as a transmission range. It has been found that electromechanical systems, when used as speech aids, should have a transmission range of up to 1.5 kHz. Thus, to make it possible to reach such a transmission range, the drive unit must have a relatively high self-resonance. A higher self-resonance, however, will also mean a "stiffer" support with a resultant reduced resiliency which in turn will cause a reduced swing for which a large force is required.

The physical interrelationship can be split by using, for the centering of the drive unit, an elastic, resilient unit such as e.g. one or a plurality of (coil) springs. This unit represents a complex system of resiliency and additional self-resonance (caused by the springs), the self-resonance being all the larger the larger the bias of the springs is.

The dynamic mass of the electromechanical converter in combination with the high resiliency of the springs constitutes a low-tuned system, allowing for large swings. In the range towards high frequencies, the self-resonances of the springs will provide for a continuously increasing acceleration and thus for an approximately constant swing which otherwise cannot be reached above the low self-resonance of the system.

If, for instance, two springs are used for centering the increase of the acceleration towards higher frequencies will be the larger the closer the self-resonant frequencies of the springs are to each other. Thus, when using two springs which e.g. have a respective self-resonance of about 1.5 kHz in the assembled state, one will obtain, in the range of 1.5 kHz—depending on the mechanical coupling of the two oscillatory systems—two resonance peaks in the range of 1.4 kHz and 1.6 kHz. Up to 1.4 kHz, one will thus obtain an approximately constant swing although the drive system is operated above its resonant frequency which can be e.g. 200 Hertz. When using conventional centering elements which normally present only one resiliency to the drive system, the above behavior which can be effected by the invention will not be possible. Only by the arrangement provided by the invention, it is made possible, with or without impedance converter, to introduce a relatively large swing of a relatively large frequency range into the human throat tissue.

The above outlined technical context can be summed up as follows:

For a speech aid, a largest possible constant swing across a largest possible frequency range is required.

A constant swing, however, is available only below the self-resonance of the electromechanical converter (drive unit), which means that, in a conventional arrangement, the self-resonance of the drive unit will form the upper limiting frequency of the transmission range of the overall electromechanical system.

Thus, to be able to obtain useful performances, there is needed a largest possible swing on the side of the overall electromechanical system The resiliency of the support of the drive system will determine the self-resonance and the swing of the system, wherein it is to be observed that a soft support will result in a large swing with low self-resonance and a hard support will result in a small swing with high self-resonance.

Spring elements and particularly coil springs have a resiliency (which can be influenced via the dynamic mass) as well as a self-resonance (which can be influenced via the bias).

By suitable selection of the spring properties, the dynamic masses and the biases, the interrelationship between the self-resonance and the stiffness of the support (the drive)—which interrelationship had been indissoluble in conventional converter technology—is dissolved. This allows for the designing of an overall electromechanical system which has a large swing while having a large self-resonance.

The invention claimed is:

1. An electromechanical system for the stimulating of vibration of biological tissue, particularly of the human throat tissue, said system comprising
    an electromechanical converter (12) having a self-resonant frequency and being operative for converting electric energy into mechanical energy at a linearly movable, driven element (14) arranged to oscillate about a zero-point position or from a zero-point position into a positive or negative direction, and
    a vibration surface (20) for acting on the biological tissue, the driven element (14) of the electromechanical converter (12) being operatively coupled to the vibration surface (20) and being supported by an elastic, resilient unit (24) having a self-resonant frequency above the self-resonant frequency of the electromechanical converter (12), whereby the vibration surface (20) is caused to oscillate across a frequency range of which the upper limit is above the self-resonant frequency of the electromechanical converter (12) and is equal to or smaller than the self-resonant frequency of the elastic, resilient unit (24), the oscillation of the vibration surface being performed with a swing which at a constant input voltage is substantially constant across the frequency.

2. The electromechanical system according to claim 1, characterized in that the elastic, resilient unit (24) is coupled, with a mechanical bias for biasing the driven element (14) in the direction towards the vibration surface (20), to the driven element (14) of the electromechanical converter (12).

3. The electromechanical system according to claim 1, characterized in that the elastic, resilient unit (24) comprises at least one spring element (26,28) coupled to the driven element (14) of the electromechanical converter (12) and extending between the driven element (14) and a fixed point externally of the electromechanical converter (12).

4. The electromechanical system according to claim 3, characterized in that the spring element is a coil spring (26, 28).

5. The electromechanical system according to claim 1, characterized in that the elastic, resilient unit (24) comprises a first spring element (26) and a second spring element (28) which are coupled to each other, at least one of the spring elements (26,28) serving to bias the driven element (14) of the electromechanical converter (12).

6. The electromechanical system according to claim 1, characterized in that the vibration surface (20) is formed on the driven element (14) or that the driven element (14) is coupled, or particularly connected, to the vibration surface (20) or to an element (50) having the vibration surface (20) formed thereon.

7. The electromechanical system according to claim 1, characterized in that the driven element (14) of the electromechanical converter (12) and the vibration surface (20) have arranged therebetween an impedance converter (22) for adapting the amount of the oscillating swing of the vibration surface (20) to the biological tissue, wherein the impedance converter (22) can be excited at its input side by the driven element (14) and on its output side will in turn excite the vibration surface (20).

8. The electromechanical system according to claim 7, characterized in that the input side of the impedance converter (22) comprises an excitable input surface (36) and the output side of the impedance converter (22) comprises an excitable output surface (38), which faces are operatively coupled to each other by an incompressible fluid such as e.g. a gas, a liquid, a gel, a silicone, another viscous medium or another material which is incompressible in the transmission range of interest.

9. The electromechanical system according to claim 8, characterized in that the input and output surfaces (36,38) of the impedance converter (22) have different sizes.

10. The electromechanical system according to claim 1, characterized in that the vibration surface (20) is rigid or elastic.

11. The electromechanical system according to claim 1, characterized in that the driven element (14) is spaced apart from the vibration surface (20) or, if provided, from the impedance converter (22) if the vibration surface (20) is unloaded or does not bear on the tissue with sufficient force.

12. Use of an electromechanical system according to claim 1 by a person who underwent laryngectomy or tracheotomy, for generating speech sounds by applying the vibration surface (20) to the throat tissue of the person in such a manner that the driven element (14) is coupled to the vibration surface (20).

13. A method for generating speech sounds, to be used by a person who underwent laryngectomy or tracheotomy, said method comprising:
    applying an electromechanical system according to claim 1 by its vibration surface (20) to the throat tissue of the person in such a manner that the driven element (14) is coupled to the vibration surface (20), and
    forming the mouth cavity and/or moving the mouth, lips and tongue by the person in a suitable manner for generating speech sounds.

* * * * *